United States Patent [19]

Cohen

[11] 4,189,439

[45] Feb. 19, 1980

[54] PROCESS OF THE PREPARATION OF HYDROXYFURENONES

[75] Inventor: Amnon M. Cohen, Amersfoort, Netherlands

[73] Assignee: Polak's Frutal Works, B.V., Amersfoort, Netherlands

[21] Appl. No.: 931,707

[22] Filed: Aug. 7, 1978

Related U.S. Application Data

[62] Division of Ser. No. 879,307, Feb. 21, 1978, Pat. No. 4,127,592.

[30] Foreign Application Priority Data

Mar. 31, 1977 [GB] United Kingdom ............... 13636/77
Dec. 20, 1977 [GB] United Kingdom ............... 52936/77

[51] Int. Cl.$^2$ ........................................... C07D 307/68
[52] U.S. Cl. ................................................. 260/347.5
[58] Field of Search ................ 260/347.3, 347.4, 347.5

[56] References Cited

U.S. PATENT DOCUMENTS

3,853,918  12/1974  van den Ouweland ...... 260/347.4 X

OTHER PUBLICATIONS

V. Euler et al, Chemical Abstracts, vol. 51 (1957), 6602a.

*Primary Examiner*—Richard Raymond
*Attorney, Agent, or Firm*—William S. Alexander

[57] ABSTRACT

A novel technique for the preparation of 4-hydroxy-5-alkyl-3-oxo-2H-furans is disclosed wherein the reaction product of an alpha-alkyl diglycolic acid diester and an oxalic acid diester is cyclized, hydrolyzed and decarboxylated. Alternatively, the corresponding 2,5-dialkyl product can be prepared by an intermediate alkylation step.

4 Claims, 1 Drawing Figure

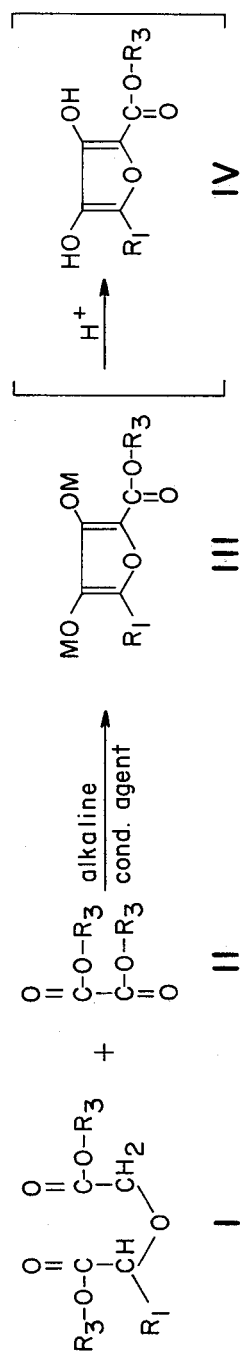
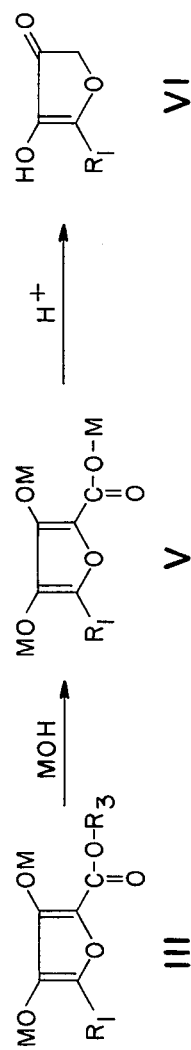
SCHEME A
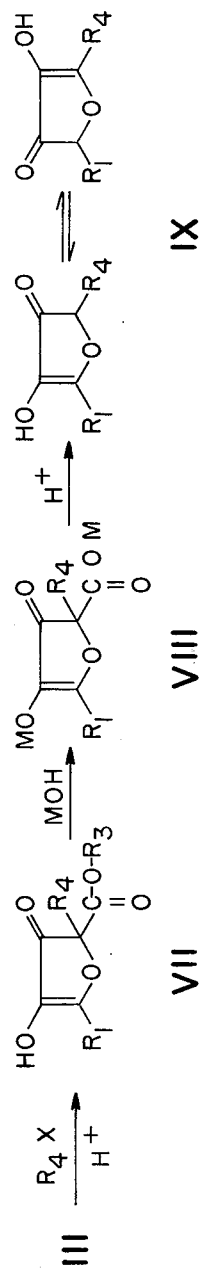
SCHEME B

PROCESS OF THE PREPARATION OF HYDROXYFURENONES

This is a division of application Ser. No. 879,307, filed Feb. 21, 1978, now U.S. Pat. No. 4,127,592.

The present invention relates to a novel process for preparing 4-hydroxy-5-alkyl-3-oxo-2H-furans and 4-hydroxy-2,5-dialkyl-3-oxo-2H-furans having the general formula:

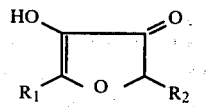

or tautomeric forms thereof where $R_1$ represents an alkyl radical having 1 to 6 carbon atoms and $R_2$ represents hydrogen or an alkyl radical having 1 to 4 carbon atoms. The invention furthermore relates to novel intermediates used in the said process.

In recent years furan derivatives of the above type have received considerable attention from researchers interested in the flavoring art. A survey of the literature reveals that these compounds are useful in a very wide range of foodstuff and beverage applications. For example, U.S. Pat. No. 3,647,825 states that 4-hydroxy-5-methyl-3-oxo-2H-furan has been added with beneficial results to bread, biscuits, candy, chocolate, meat and processed meat, milk products, processed food prepared from eggs, fresh and smoked fish and vegetable, also to powdered soup concentrates, dried fruits and nuts, canned fruits, soft drinks, liqueur, wine, whiskey, instant coffee, but also cigars and cigarettes, chewing gum and oral hygiene preparations such as toothpastes, mouth washes and mouth wash concentrates.

U.S. Pat. No. 3,887,589 teaches the use of 2,5-diethyl-4-hydroxy-3-oxo-2H-furan in bakery products to provide a more pleasant taste and a fresher impression. U.S. Pat. No. 3,576,014 teaches using 4-hydroxy-2-methyl-5-ethyl-3-oxo-2H-furan and 4-hydroxy-2-ethyl-5-methyl-3-oxo-2H-furan as a raspberry or gooseberry flavoring. U.S. Pat. No. 3,709,697 teaches 4-hydroxy-2-methyl-5-ethyl-3-oxo-2H-furan and 4-hydroxy-2,5-diethyl-3-oxo-2H-furan as additives to impart or enhance a meat flavor.

Many syntheses have been suggested for the preparation of furans of the above-identified type. However, all of these are either non-economical multistep laboratory methods which cannot profitably be applied to the production of the compounds on a commercial scale or they utilize very expensive natural products such as rhamnose (cf. Proc.Am.Soc. Brewing Chemists 84, (1963)) which can be obtained only in small insufficient quantities of unpredictable quality and which therefore are not suitable starting materials for production of the furans on a commercial scale. For techniques which have heretofore been proposed for preparing these compounds, reference can be had to J.Org.Chem. 31, 2391-4 (1966), J. Org. Chem. 38, 123-125 (1973), and to U.S. Pat. Nos. 3,709,697; 3,647,825; 3,887,589; 3,576,014; 3,694,466; 3,651,097; 3,853,918; 3,629,292; and 3,629,293; British Pat. No. 1,440,270; Swiss Pat. No. 565,168.

In accordance with this invention, it has now been found that furan derivatives of the class above designated can be prepared in a technically very simple and commercially feasible manner.

The novel process of this invention comprises the steps (a) condensing a dialkyl-α-alkyl diglycolic acid ester with an oxalic acid diester in the presence of an alkaline condensing agent to prepare the disodium salt of 2-carbalkoxy-3,4-dihydroxy-5-alkyl furan;

(b) hydrolyzing the carbalkoxy group of said disodium salt;

(c) decarboxylating the hydrolyzed product; and (d) recovering 4-hydroxy-5-alkyl-3-oxo-2H-furan.

Optionally, the disodium salt of 2-carbalkoxy-3,4-dihydroxy-5-alkyl furan can be alkylated to a 2,5-dialkyl homologue by alkylating it with a lower alkyl halide prior to the hydrolysis step.

The process of the invention is represented schematically by the reaction schemes diagrammed in the drawing where $R_1$ has the meaning specified above, $R_3$ is an alkyl radical having 1 to 4 carbon atoms, $R_4$ is an alkyl radical fitting the description of the alkyl radical represented by $R_2$ above, M is an alkali metal ion and X is a halogen.

Starting materials I and II are easily prepared compounds. Compound I as a dialkyl α-alkyl diglycolic acid ester. It can be prepared by reaction of an alkyl haloacetate (bromo- or chloro-) and an alkyl ester of an α-hydroxy carboxylic acid. This synthesis is described by A. Soladie-Cavallo and P. Vieles in Bull.Soc.Chim.-France, 1967, page 517 et seq. The diethyl and dimethyl esters are preferred. Dialkyl oxolates (II) are cheap, commercially available compounds. The diethyl and dimethyl esters are very common and are accordingly preferred for use in the reaction. Other lower alkyl esters can, however, be used with equally good results.

The reaction between the alpha-alkyl diglycolic acid diester and the dialkyl oxalate produces the disodium salt of 2-carbalkoxy-3,4-dihydroxy-5-alkyl furan, III. The reaction is carried out in an inert diluent or solvent in the presence of an alkaline condensing agent, preferably an alkali metal alkoxide of a 1 to 4 carbon alcohol or an alkali metal hydride. Condensing agents based on any of the alkali metals e.g. lithium, potassium and sodium, can be used. The preferred alkaline condensing agents are sodium methoxide, sodium ethoxide, and sodium hydride. Some of the intermediate compounds of the reaction are sometimes referred to hereinafter as sodium salts. It should be understood that these compounds could equally well be other alkali metal salts.

By an inert diluent or solvent is meant an organic liquid which does not itself enter into the reaction or which cannot react in another way with the other reactants. The diluent can be either polar or non polar. Thus there can be used such organic liquids as aliphatic and aromatic hydrocarbons, alcohols, dimethyl formamide, dimethyl sulfoxide, ethers, and nitriles. The choice of diluent can affect the temperature at which the reaction is carried out but necessary conditions for a particular diluent are easily determined experimentally.

In carrying out reaction scheme A equimolar quantities of the dialkyl-α-alkyl diglycolic acid ester and the dialkyl oxalate, I and II, are added to a solution or suspension of two equivalents of the alkaline condensing agent in the inert diluent at low temperature. Reaction begins substantially immediately upon contact of reagents I and II. It is preferable to remove the alcohol formed by the condensation reaction as the reaction proceeds as this helps to force the reaction to completion, resulting in better yields. This is not critical to the formation of the intermediate disodium salt of 2-carbalkoxy-3,4-dihydroxy-5-alkylfuran. When the reaction is complete, the disodium salt can be recovered as such, acidified to its 3,4-dihydroxy form and recovered or subjected immediately to the hydrolysis and decarboxylation steps to convert it to 4-hydroxy-5-alkyl-3-oxo-2H-furan or it can be used in reaction scheme B without any intermediate recovery operations.

In carrying out reaction scheme B in which the intermediate compound III is alkylated to form a 2,5-dialkyl substituted product the solvents or diluents used in scheme A can be used, but it is preferable to employ a dipolar, aprotic diluent or solvent. The reaction proceeds more rapidly in the presence of such a solvent. Dimethyl sulfoxide, dimethylformamide, or a mixture of at least about 10% or more by weight of one of these in toluene or another polar or apolar organic liquid is preferred.

Prior to carrying out the alkylation, it is helpful to convert the disodium salt to the monosodium salt by adding the calculated amount of an anhydrous organic acid or a mineral acid to the reaction mixture. The monosodium salt has been found to be more soluble in the organic reaction medium and the alkylation reaction proceeds more rapidly and more selectively when carried out on this salt than with the disodium salt.

The alkylation reaction is carried out using an equimolar amount, based on compound III of an alkyl halide of 1 to 4 carbon atoms. Any alkyl halide fitting this description can be used, e.g. the alkyl chlorides, alkyl bromides, and alkyl iodides. The reaction can be conducted at about 20° to 80° C. and takes place in about 1 to 20 hours depending upon the temperature. Completion of the alkylation reaction is indicated by a steady pH reading of about 6.5 to 7.5.

As mentioned above in the case of compound III, the initial alkylation product VII, can be recovered as such, or subjected immediately to the hydrolysis and decarboxylation steps without any intermediate recovery steps.

Conversion of the intermediate compounds to their intended final products is effected in the same way for both reaction schemes A and B. In each case, the ester is hydrolyzed to its alkali salt form and thereafter decarboxylated.

Hydrolysis of the ester can be carried out by the use of an alkali metal hydroxide in a manner known to the art for effecting hydrolysis of an ester. The resulting de-esterified carboxylic acid group is not stable and decarboxylation takes place spontaneously upon neutralization or acidification thereof.

As suggested hereinabove, the intermediate reaction products IV and VII can be isolated and recovered if desired. These can be further processed as described hereinabove at a later time by hydrolyzing and decarboxylating as described. In particular, it is useful to recover product IV in the intermediate state as it can thereafter be used to prepare either the alkylated final product as needed.

These intermediate products, 2-carbalkoxy-3,4-dihydroxy-5-alkyl furan (IV) which may exist to a small extent in its keto-enol tautomeric forms, and 2-carbalkoxy-4-hydroxy-2,5-dialkyl-3-oxo-2H-furan (VII) are novel compounds. In addition to their utility as intermediates in the instant process, they have been found to be useful additives to several types of flavors because of their ability to enhance the sweetness causing a richer, more balanced taste by improving the body notes. In this respect they are useful in a variety of applications such as e.g. pastries, soft drinks, confectionaries, and as components of artificial sweetener compositions. The following examples illustrate the invention.

EXAMPLE 1

2-Carbethoxy-5-methyl-3,4-dihydroxy-furan

In a 6-L three-necked flask fitted with a mechanical stirrer, a dropping funnel, a thermometer, a 30 cm Vigreux column connected to a deflegmator and a gas inlet tube, is placed a suspension of 408 g of sodium ethoxide in 3 L of dry toluene. To the stirred suspension is added, under nitrogen, at 0° C., 438 g of diethyl oxalate over a period of 75 minutes. To the yellow reaction mixture is then added, at 0°–2° C., 612 g of diethyl α-methyldiglycolate (A. Solladie-Cavallo and P. Vieles, Bull. Soc. Chim. France 1967, 517), over a period of 90 minutes. The reaction mixture is stirred at room temperature for an additional 2 hours. The reaction mixture is then warmed up gradually and an ethanol-toluene mixture is distilled off till the vapour temperature reaches 107° C. The reaction mixture is cooled to room temperature and stirred for 30 minutes with 2 L of water. The reaction mixture is transferred to a separatory funnel, the toluene layer is separated off and the water layer is washed successively with diisopropyl ether and pentane. The aqueous solution is acidified with concentrated hydrochloric acid. The temperature is maintained at 0° C. throughout the acidification. The solid product is filtered off and dried, yielding 425 g 76% of 2-carbethoxy-5-methyl-3,4-dihydroxy furan; recrystallized from alcohol, m.p. 120°–121° C.

NMR ($CDCl_3$), δ 1.40 (3H, t), 2.28 (3H, s), 4.40 (2H, q), 6.0 (2H, broad).

EXAMPLE 2

2-Carbethoxy-5-methyl-3,4-dihydroxy furan

In a 2 L three-necked flask fitted with a mechanical stirrer, a thermometer, a nitrogen inlet tube and a reflux condensor protected by a calcium chloride tube, is placed a solution of 102 g of diethyl α-methyldiglycolate and 73 g of diethyl oxalate in 1 L of dry dimethylformamide. To the stirred reaction mixture is added at room temperature 24 g of sodium hydride and 0.5 ml of ethanol. The reaction mixture is then heated under nitrogen to 90° C. when an exothermic reaction accompanied by hydrogen evolution is observed. The temperature is maintained at 110° C. for an additional 15 minutes. The reaction mixture is cooled then to room temperature and the solvent is removed under vacuum. The residue is dissolved in water and the aqueous solution is acidified with concentrated hydrochloric acid. The temperature is maintained at 0° C. throughout the acidification. The solid product is filtered off and dried.

Yielding 39.5 g (42.5%) of 2-carbethoxy-5-methyl-3,4-dihydroxy furan m.p. 119°–120° C.

EXAMPLE 3

4-Hydroxy-5-methyl-3-oxo-2H-furan

A solution of 37.2 g of 2-carbethoxy-5-methyl-3,4-dihydroxy furan and 32 g of sodium hydroxide in 450 ml of water is kept at room temperature, under nitrogen, for 20 hours.

The reaction mixture is acidified (pH3) with concentrated hydrochloric acid, then stirred at 50° C. for 4 hours, and continuously extracted for 6 hours with ether. The ether extract is dried and concentrated under vacuum until the total volume of the solution is reduced to about 50 ml. The ether solution is cooled to −70° C. and filtered. The solid product is washed with pentane and dried, yielding 13 g (57%) of 4-hydroxy-5-methyl-3-oxo-2H-furan, recrystallized from alcohol-ether, m.p. 128.2°–129.6° C.

NMR (CDCl$_3$), δ 2.26 (3H, t), 4.52 (2H, q), 6.9 (1H, broad).

EXAMPLE 4

4-Hydroxy-5-methyl-3-oxo-2H-furan

In a 4 L three-necked flask fitted with a mechanical stirrer, a dropping funnel, a thermometer, a 30 cm Vigreux column connected to a deflegmator and a gas inlet tube, is placed a suspension of 408 g of sodium ethoxide in 3 L of dry toluene. To the stirred suspension is added, under nitrogen, at 0°–5° C., 438 g of diethyl oxalate over a period of 75 minutes. To the yellow reaction mixture is then added, at 4°–6° C., 612 g of diethyl α-methyldiglycolate over a period of 90 minutes. The reaction mixture is stirred at room temperature for an additional two hours. The reaction mixture is then warmed up gradually and the ethanol toluene mixture is distilled off till the vapour temperature reaches 107° C. The reaction is then cooled to room temperature and stirred for 30 minutes with 2 L of water. The reaction mixture is transferred to a separatory funnel, the toluene layer is separated off and the water layer is washed with ether. After an addition of 240 g of sodium hydroxide the aqueous layer is kept at room temperature, under nitrogen, for 20 hours. The reaction mixture is acidified (pH3) with concentrated hydrochloric acid, then stirred at 30° C. for 2 hours and continuously extracted for 10 hours with ether. The ether extract is dried and the solvent is removed under vacuum. The solid residue is recrystallized from ethanol yielding 243 g (71%) of 4-hydroxy-5-methyl-3-oxo-2H-furan, m.p. 130°–130.5° C.

EXAMPLE 5

4-Hydroxy-5-methyl-3-oxo-2H-furan

Example 4 is repeated substituting dimethyl oxalate for diethyl oxalate and dimethyl α-methyldiglycolate for diethyl α-methyldiglycolate. There is obtained 253 g (74%) of 4-hydroxy-5-methyl-3-oxo-2H-furan, m.p. 129.5°–130° C.

EXAMPLE 6

4-Hydroxy-5-methyl-3-oxo-2H-furan

In a 2 L three-necked flask fitted with a mechanical stirrer, a dropping funnel, a thermometer and reflux condenser is placed a solution of 108 g of sodium methoxide in 500 ml of methanol. To the stirred solution is added at 0°–10° C., 146 g of diethyl oxalate over a period of 30 minutes. To the reaction mixture is then added at 0°–10° C. 204 g of diethyl α-methyldiglycolate over a period of 120 minutes. The reaction mixture is then stirred at reflux temperature for an additional 13 hours. The solvent is distilled off and the residue is dried at 100° C. under vacuum. The dried residue is dissolved in 600 ml of 15% sodium hydroxide solution. The basic solution is kept at room temperature for 20 hours. The reaction mixture is then acidified and continuously extracted with ether. The ether extract is dried and the solvent is removed under vacuum. The solid residue is recrystallized from alcohol yielding 69 g (60%) of 4-hydroxy-5-methyl-3-oxo-2H-furan, m.p. 130°–130.5° C.

EXAMPLE 7

2-Carbethoxy-2,5-dimethyl-3-oxo-4-hydroxy-2H-furan

In a 0.5 L three-necked flask fitted as described in Example 1, is placed a suspension of 27.2 g of sodium ethoxide in 180 ml of dry toluene and 20 ml of dry dimethylformamide. To the stirred suspension is added at 0° C. 29.2 g of diethyl oxalate over a period of 15 minutes. To the yellow reaction mixture is then added at 0°–5° C. 40.8 g of diethyl α-methyldiglycolate over a period of 15 minutes. The reaction mixture is stirred at room temperature for an additional 30 minutes. The reaction mixture is then warmed up gradually and the ethanol-toluene mixture is distilled off till the vapour temperature reaches 107° C. The reaction mixture is then cooled to 0° C. and 9.2 g of formic acid is added followed by a solution of 9.2 g ethanol and 0.5 g of sodium iodide in 60 ml of dimethyl formamide. Gaseous methyl bromide is bubbled through the vigorously stirred reaction mixture at 40°–50° C. till the pH of the reaction mixture reaches 7.0–7.5. The solvents are removed under vacuum (complete removal of the dimethyl formamide is essential for an optimal isolation of the solid product) and the residue is dissolved in ether. The sodium bromide is filtered off, the ether solution is concentrated under vacuum and pentane is added to the concentrated ether solution. The ether-pentane solution is cooled and filtered. The solid product is washed with pentane and dried, yielding 24 g (70%) of 2-carbethoxy-2,5-dimethyl-3-oxo-4-hydroxy-2H-furan, recrystallized from cyclohexane. M.p. 89.2°–89.5° C.

NMR (CDCl$_3$), δ 1.27 (3H, t), 1.65 (3H, s), 2.32 (3H, s), 4.22 (2H, q), 6.00 (1H, broad).

EXAMPLE 8

2-Carbethoxy-2,5-dimethyl-3-oxo-4-hydroxy-2H-furan

Example 7 is repeated substituting methyl iodide for methyl bromide. There is obtained 22 g (64%) of 2-carbethoxy-2,5-dimethyl-3-oxo-4-hydroxy-2H-furan. M.p. 89.8°–90.2° C.

EXAMPLE 9

2-Carbethoxy-2,5-dimethyl-3-oxo-4-hydroxy-2H-furan

Example 7 is repeated substituting methyl chloride for methyl bromide. There is obtained 23 g (67%) of 2-carbethoxy-2,5-dimethyl-3-oxo-4-hydroxy-2H-furan. M.p. 89.7°–90° C.

EXAMPLE 10

2-Carbethoxy-2,5-dimethyl-3-oxo-4-hydroxy-2H-furan

In a 250 ml three-necked flask fitted with a mechanical stirrer and a gas inlet tube is placed a solution of 3.4 g of sodium ethoxide in 100 ml of ethanol. To the stirred solution is added at room temperature, under nitrogen, 9.3 g of 2-carbethoxy-5-methyl-3,4-dihydroxy-furan and 0.5 g of sodium iodide. Gaseous methyl bromide is bubbled through the vigorously stirred reaction mixture at 50°–60° C. till the pH of the reaction mixture reaches 6.5–7.0. The solvent is removed under vacuum and the residue is dissolved in ether. The sodium bromide is filtered off, the ether solution is concentrated under vacuum and the residue is distilled through a short Vigreux column; 2-carbethoxy-2,5-dimethyl-3-oxo-4-hydroxy-2H-furan is collected at 102°–105° C./0.2 mm.

Yield 8.1 g (81%), recrystallized from cyclohexane, m.p. 89.8°–90.1° C.

EXAMPLE 11

4-Hydroxy-2,5-dimethyl-3-oxo-2H-furan

A solution of 9 g of 2-carbethoxy-2,5-dimethyl-3-oxo-4-hydroxy-2H-furan and 5.4 g of sodium hydroxide in 50 ml of water is kept at room temperature under nitrogen for 20 hours. The reaction mixture is acidified with hydrochloric acid, then stirred at 30° C. for an hour and continuously extracted for 6 hours with ether. The ether extract is dried and the solvent is removed under vacuum, the residue is dissolved in a mixture of 5 ml of dry ether and 5 ml of dry pentane. The solution is cooled to −10° C. and filtered. The solid product is dried, yielding 4.1 g (70%) of 4-hydroxy-2,5-dimethyl-3-oxo-2H-furan. The isolated product is identical (NMR and IR) with a sample of 4-hydroxy-2,5-dimethyl-3-oxo-2H-furan prepared from rhamnose (loc cit). M.p. 82°–84° C.

EXAMPLE 12

4-Hydroxy-2,5-dimethyl-3-oxo-2H-furan

In a 20 L three-necked flask fitted with a mechanical stirrer, a dropping funnel, a thermometer, a nitrogen inlet tube and a 30 cm Vigreux column connected to a deflegmator, is placed a suspension of 1512 g of sodium methoxide in 10.5 L of dimethyl formamide. To the stirred suspension is added, under nitrogen, at 5° C., 2044 g of diethyl oxalate over a period of 90 minutes. To the yellow reaction mixture is then added, at 2°–5° C., 2856 g of diethyl 2-methyl-diglycolate over a period of 3 hours. The reaction mixture is stirred at room temperature for an additional 3 hours. The reaction mixture is then warmed up gradually to 90°–100° C. and kept at that temperature till the alcohol distillation ceases. The reaction mixture is cooled to room temperature and 649 g of formic acid is added. Methyl bromide is then bubbled through the reaction mixture at 40°–50° C. till the pH of the reaction mixture reaches 7.0–7.5. The solvents are removed under vacuum and the residue is dissolved in a solution of 2472 g of sodium hydroxide in 9 L of water. The reaction mixture is kept at room temperature under nitrogen for 20 hours, acidified with hydrochloric acid and then continuously extracted with ether. The ether extract is dried and the solvent is removed under vacuum, the residue is recrystallized from ether yielding 916 g (51%) of 4-hydroxy-2,5-dimethyl-3-oxo-2H-furan, m.p. 80°–82° C.

The isolated product is identical (NMR and IR) with a sample of 4-hydroxy-2,5-dimethyl-3-oxo-2H-furan prepared from rhamnose (loc cit).

EXAMPLE 13

4-Hydroxy-2,5-dimethyl-3-oxo-2H-furan

Example 12 is repeated replacing the formic acid by hydrogen chloride. There is obtained 4-hydroxy-2,5-dimethyl-3-oxo-2H-furan in 48% yield, m.p. 80°–82° C.

EXAMPLE 14

4-Hydroxy-2,5-dimethyl-3-oxo-2H-furan

In a 1 L three-necked flask fitted with a mechanical stirrer and a gas inlet tube is placed a suspension of 34 g of sodium ethoxide in a mixture of 100 ml of dimethylformamide and 300 ml of toluene. To the stirred suspension is added at room temperature, under nitrogen, 93 g of 2-carbethoxy-5-methyl-3,4-dihydroxy-furan. Gaseous methyl bromide is bubbled through the stirred reaction mixture at 30°–40° C. till the pH of the reaction mixture reaches 6.5–7.0. The solvents are removed under vacuum and the residue is dissolved in a solution of 80 g of sodium hydroxide in 350 ml of water. The reaction mixture is kept at room temperature under nitrogen for 20 hours, acidified with hydrochloric acid and continuously extracted with ether. The ether extract is dried and the solvent removed under vacuum, the residue is recrystallized from ether, yielding 41.5 g (65%) of 4-hydroxy-2,5-dimethyl-3-oxo-2H-furan, m.p. 81.5°–83.1° C.

EXAMPLE 15

4-Hydroxy-2-methyl-5-ethyl-3-oxo-2H-furan and 4-hydroxy-2-ethyl-5-methyl-3-oxo-2H-furan In a 1 L three-necked flask fitted with a mechanical stirrer, a dropping funnel, a thermometer, a nitrogen inlet tube and a reflux condenser protected by a calcium chloride tube is placed a suspension of 20.4 g of sodium ethoxide in 180 ml of toluene and 120 ml of dimethylformamide. To the stirred reaction mixture is added 55.8 g of 2-carbethoxy-5-methyl-3,4-dihydroxy furan. The temperature is maintained below 20° C. throughout the addition. To the clear red solution is added 120 g of ethyl bromide over a period of 15 minutes. The reaction mixture is then stirred at 40° C. for an additional 20 hours. The solvents are removed under vacuum and the residue is dissolved in ether. The sodium bromide is filtered off and the ether solution is extracted with cold 5% sodium hydroxide solution. The aqueous solution is acidified with hydrochloric acid. The temperature is maintained at 0° C. throughout the acidification. The acidified aqueous solution is then continuously extracted for 6 hours with ether. The ether extract is dried, the solvent is removed under vacuum and the residue is distilled through a short Vigreux column. The product is collected as an isomeric mixture of 4-hydroxy-2-methyl-5-ethyl-3-oxo-2H-furan (40%) and 4-hydroxy-2-ethyl-5-methyl-3-oxo-2H-furan (60%) at 74°–76° C./0.3 mm. Yield 15 g (35%), $n_D^{20}$ 1.5096.

NMR (CCl$_4$) δ 0.99 (t), 1.37 (t), 1.85 (m), 2.25 (s), 2.65 (q), 4.38 (m), 7.2 (broad s).

EXAMPLE 16

4-Hydroxy-2-methyl-5-hexyl-3-oxo-2H-furan and 4-hydroxy-2-hexyl-5-methyl-3-oxo-2H-furan In a 1 L three-necked flask fitted with a mechanical stirrer, a dropping funnel, a thermometer, a nitrogen inlet tube and a reflux condensor protected by a calcium chloride tube, is placed a suspension of 19.8 g of sodium ethoxide in 130 ml of dry toluene and 15 ml of dry dimethylformamide. After stirring for 10 minutes 21.3 g of diethyl oxalate is added dropwise, under nitrogen, at 10° C. To the yellow reaction mixture is then added dropwise, at 10°–15° C., 40 g of diethyl α-hexyldiglycolate (prepared according to A. Solladie-Cavallo and P. Vieles, Bull. Soc. Chim. France, 1967, 517; bp. 112° C./0.3 mm, $n_D^{20}$ 1.4345). The reaction mixture is stirred at room temperature for an additional 15 minutes and then warmed up gradually. The ethanol-toluene mixture is distilled off till the vapour temperature reaches 110° C. The reaction mixture is then cooled to 0° C. and 6.9 g of formic acid is added followed successively by 6.9 g of ethanol and 100 ml of dimethyl formamide. Gaseous methyl bromide is bubbled through the vigorously stirred reaction mixture at 25°–40° C. till the pH of the reaction mixture reaches 7.0–7.5. The solvents are removed completely under vacuum and the residue is dissolved in 200 ml of ether and 24.5 g of sodium hydroxide in 100 ml of water. The resulting slurry is stirred at room temperature under nitrogen for 20 hours. The mixture is then acidified with hydrochloric acid (pH=3.4). The temperature is maintained at 20° C. throughout the acidification. The acidified aqueous solution is neutralised with a 10 N sodium hydroxide solution in water till the pH reaches 6.8, then continuously extracted for 6 hours with ether. The ether extract is dried and the solvent is removed under vacuum. The residue is distilled through a short Vigreux column. The product is collected as an isomeric mixture of 4-hydroxy-2-methyl-5-hexyl-3-oxo-2H-furan (55%) and 4-hydroxy-2-hexyl-5-methyl-3-oxo-2H-furan (45%) at 102° C./0.1 mm. Yield is 12.5 g (42%), $n_D^{20}$=1.4935.

NMR (CDCl$_3$) δ 0.9, 1.45 (d), 2.28 (d), 2.6 (t), 4.5 (m), 7.3 (broad).

EXAMPLE 17

4-Hydroxy-2-methyl-5-pentyl-3-oxo-2H-furan and 4-hydroxy-2-pentyl-5-methyl-3-oxo-2H-furan Example 16 is repeated substituting diethyl α-pentyl-diglycolate (prepared according to A. Solladie-Cavallo and P. Vieles, Bull. Soc. Chim. France, 1967, 517; b.p. 106°–108° C./0.2 mm) for diethyl α-hexyldiglycolate in stoichiometrically equivalent amounts. There is obtained in a yield of 52% a mixture of 4-hydroxy-2-methyl-5-pentyl-3-oxo-2H-furan (55%) and 4-hydroxy-2-pentyl-5-methyl-3-oxo-2H-furan (45%), b.p. 102° C./0.4 mm, $n_D^{20}$=1.4956.

NMR (CDCl$_3$) δ 0.84, 2.20 (d), 2.56 (t), 4.40 (m), 6.9 (broad).

EXAMPLE 18

4-Hydroxy-2-methyl-5-isobutyl-3-oxo-2H-furan and 4-hydroxy-2-isobutyl-5-methyl-3-oxo-2H-furan Example 16 is repeated substituting diethyl α-isobutyldiglycolate (prepared according to A. Solladie-Cavallo and P. Vieles, Bull. Soc. Chim. France, 1967, 517; b.p. 106°–110° C./0.9 mm) for diethyl α-hexyldiglycolate in stoichiometrically equivalent amounts. There is obtained in a yield of 57% a mixture of 4-hydroxy-2-methyl-5-isobutyl-3-oxo-2H-furan (67%) and 4-hydroxy-2-isobutyl-5-methyl-3-oxo-2H-furan (33%), b.p. 97° C./0.9 mm, $n_D^{20}$=1.4998.

NMR (CDCl$_3$) δ 0.98, 1.44 (d), 2.14 (d), 2.51 (d), 4.5 (m), 7.7 (broad).

EXAMPLE 19

4-Hydroxy-2-methyl-5-butyl-3-oxo-2H-furan and 4-hydroxy-2-butyl-5-methyl-3-oxo-2H-furan Example 16 is repeated substituting diethyl α-butyldiglycolate (prepared according to A. Solladie-Cavallo and P. Vieles, Bull. Soc. Chim. France, 1967, 517; b.p. 90°–91° C./0.2 mm) for diethyl α-hexyldiglycolate in stoichiometrically equivalent amounts. There is obtained in a yield of 40% an isomeric mixture of 4-hydroxy-2-methyl-5-butyl-3-oxo-2H-furan (50%) and 4-hydroxy-2-butyl-5-methyl-3-oxo-2H-furan (50%), b.p. 104° C./0.7 mm, $n_D^{20}$=1.4998.

NMR (CDCl$_3$) δ 0.95 (3H), 1.44 (d), 2.25 (d), 2.60 (t), 4.43 (m), 6.9 (broad).

EXAMPLE 20

4-Hydroxy-2-methyl-5-ethyl-3-oxo-2H-furan and 4-hydroxy-2-ethyl-5-methyl-3-oxo-2H-furan Example 16 is repeated substituting diethyl α-ethyldiglycolate (prepared according to A. Solladie-Cavallo and P. Vieles, Bull. Soc. Chim. France, 1967, 517; b.p. 80°–81° C./0.2 mm, $n_D^{20}$=1.4255) for diethyl α-hexyldiglycolate in stoichiometrically equivalent amounts. There is obtained, in a yield of 46%, an isomeric mixture of 4-hydroxy-2-methyl-5-ethyl-3-oxo-2H-furan (38%) and 4-hydroxy-2-ethyl-5-methyl-3-oxo-2H-furan (62%), $n_D^{20}$=1.5111, b.p. 80°–82° C./0.6 mm.

EXAMPLE 21

4-Hydroxy-5-ethyl-3-oxo-2H-furan

In a 1 L three-necked flask fitted with a mechanical stirrer, a dropping funnel, a thermometer, a nitrogen inlet tube and a reflux condensor protected by a calcium chloride tube, is placed a suspension of 25.2 g of sodium ethoxide in 185 ml of dry toluene. After stirring for 15 minutes, 27.1 g of diethyl oxalate is added under nitrogen at 10° C. dropwise. To the yellow reaction mixture is then dropwise added at 10°–15° C., 40.5 g of diethyl α-ethyldiglycolate (prepared according to A. Solladie-Cavallo and P. Vieles, Bull. Soc. Chim. France, 1967, 517; b.p. 80°–81° C./0.2 mm, $n_D^{20}$=1.4255). The reaction mixture is stirred at room temperature for an additional 12 hours. The reaction mixture is then warmed up gradually and the ethanol-toluene mixture is distilled off till the vapour temperature reaches 104° C. The reaction is then cooled to room temperature and stirred for 30 minutes with 200 ml of water. The reaction mixture is then transferred to a separatory funnel, the toluene layer is separated off. To the aqueous layer is added successively a solution of 15.2 g of sodium hydroxide in 200 ml of water and 100 ml of ether. This mixture is stirred at room temperature under nitrogen for 20 hours. The reaction mixture is acidified (pH=3) with concentrated hydrochloric acid, then stirred at room temperature for 2 hours. The resulting solution is neutralized with 10 N sodium hydroxide solution in water till the pH reaches 6.8, then continuously extracted for 10 hours with ether. The ether extract is dried and the solvent is removed under vacuum, giving 13.3 g of solid material. Recrystallization from ether afforded 8.3 g (35%) of 4-hydroxy-5-ethyl-3-oxo-2H-furan, m.p. 52°–54° C.

NMR (CDCl$_3$) δ 1.24 (t, 3H), 2.64 (q, 2H), 4.52 (d, 2H), 6.5 (s, 1H).

EXAMPLE 22

4-Hydroxy-5-hexyl-3-oxo-2H-furan

Example 21 is repeated substituting diethyl α-hexyl-diglycolate (prepared according to A. Solladie-Cavallo and P. Vieles, Bull. Soc. Chim. France, 1967, 517, b.p. 112° C./0.3 mm, $n_D^{20}$ 1.4345) for diethyl α-ethyldiglycolate in stoichiometrically equivalent amounts. There is obtained 61 g of solid material. Recrystallization from ether gave 20 g (30%) of 4-hydroxy-5-hexyl-3-oxo-2H-furan, m.p. 51°–52° C.

NMR (CDCl$_3$) δ 0.9 (3H), 1.3–1.8 (m, 8H), 2.60 (t, 2H), 4.49 (d, 2H), 7.1 (Broad, 1H).

EXAMPLE 23

4-Hydroxy-2,5-diethyl-3-oxo-2H-furan

In a 1 L three-necked flask fitted with a mechanical stirrer, a dropping funnel, a thermometer, a nitrogen inlet tube and a reflux condensor protected by a calcium chloride tube, is placed a suspension of 68 g of sodium ethoxide in 375 ml of DMF. To the stirred reaction mixture is added dropwise, under nitrogen, at 5° C. 73 g of diethyl oxalate. After stirring over a period of 15 minutes is then added dropwise at 5°–10° C. 109 g of diethyl α-ethyldiglycolate. The reaction mixture is stirred at room temperature for 12 hours and then the temperature is raised gradually. The ethanol is distilled off while the reaction mixture is kept at 100° C. for 6 hours. After vigorous stirring the reaction mixture turns into a thick slurry. In total, 37 g of ethanol are collected. Then the reaction mixture is cooled to 20° C. and 46 g of formic acid is added followed by 89.5 g of ethylbromide over a period of 30 minutes and 9 g of sodium iodide. The reaction mixture is then stirred at 40° C. for an additional 16 hours. The solvent is removed completely under vacuum and the residue is dissolved in a solution of 88.3 g of sodium hydroxide in 500 ml of water. The resulting slurry is stirred at room temperature under nitrogen for 3 days. The mixture is then acidified with hydrochloric acid (pH=3). The temperature is maintained at 20° C. throughout the acidification. The acidified aqueous solution is neutralized with a 10 N sodium hydroxide solution in water until the pH reaches 6.8, then continuously extracted with ether. After 6 hours the ether extract is dried and the solvent is removed under vacuum giving 43.5 g of residue. An additional period of extraction for 12 hours gives 18.5 g of material. The combined residues are distilled through a short Vigreux column yielding 27 g (35%) of 4-hydroxy-2,5-diethyl-3-oxo-2H-furan, b.p. 89° C./0.9 mm, $n_D^{20} = 1.5090$.

NMR (CDCl$_3$) δ 0.98 (t, 3H), 1.27 (t, 3H), 1.85 (m, 2H), 2.71 (q, 2H), 4.40 (m, 1H), 7.4 (broad s, 1H).

EXAMPLE 24

Two cream flavours were prepared by mixing the following ingredients:

|  | A | B |
|---|---|---|
| acetoin | 3,- | 3,- |
| diacetyl | 2,- | 2,- |
| vanilline | 2,- | 2,- |
| ethylbutyrate | 1,- | 1,- |
| maltol | 0,5 | 0,5 |
| δ-decalactone | 1,- | 1,- |
| ethyllactate | 5,- | 5,- |
| butyric acid | 5,- | 5,- |
| caproic acid | 0,5 | 0,5 |
| 2-carbethoxy-5-methyl-3,4-dihydroxy furan | — | 50,- |
| propyleen glycol | 980,- | 930,- |
|  | 1000,- | 1000,- |

Mixtures A and B were separately added to an 8% sugar solution at a level of 0.2 g per liter. The testsolutions were tasted and compared. The panel preferred the testsolution containing mixture B over the testsolution containing mixture A because the testsolution containing mixture B has a richer, sweeter and creamer character than the testsolution containing mixture A.

EXAMPLE 25

Two strawberry flavours were prepared by mixing the following ingredients:

|  | A | B |
|---|---|---|
| ethylacetate | 2,0 | 2,0 |
| ethylbutyrate | 5,0 | 5,0 |
| ethylformate | 1,5 | 1,5 |
| ethyl isovalerate | 1,0 | 1,0 |
| ethyl caproate | 0,5 | 0,5 |
| γ-undecalactone | 0,8 | 0,8 |
| ethylphenylglycidate | 10,0 | 10,0 |
| ethylbenzoate | 2,5 | 2,5 |
| dimethylanthranilate | 2,0 | 2,0 |
| methylisopropylphenylpropionaldehyde 10% sol.$^x$ | 0,5 | 0,5 |
| methyloctincarbonate 10% sol.$^x$ | 0,5 | 0,5 |
| maltol | 3,5 | 3,5 |
| acetoin | 10,0 | 10,0 |
| 2-carbethoxy-2,5-dimethyl-3-oxo-4-hydroxy-2H-furan | — | 12,5 |
| propylene glycol | 960,2 | 947,7 |
|  | 1000,0 | 1000,0 |

$^x$in propylene glycol

Mixtures A and B were separately added to a drink containing 8% sugar and 0.05% citric acid. The drinks were tasted and compared. The panel preferred the drink containing mixture B over the drink containing mixture A because the drink containing mixture B had a fuller, sweeter and more balanced strawberry character than the drink containing mixture A.

What is claimed is:

1. 2-Carbalkoxy-3,4-dihydroxy-5-alkyl-furan having the structural formula

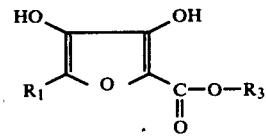

where R$_1$ represents an alkyl radical having 1 to 6 carbon atoms and R$_3$ represents an alkyl radical having 1 to 4 carbon atoms.

2. 2-Carbalkoxy-4-hydroxy-2,5-dialkyl-3-oxo-2H-furan having the structural formula

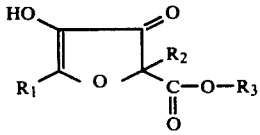

where R$_1$ represents an alkyl radical having 1 to 6 carbon atoms, R$_2$ represents an alkyl radical having 1 to 4 carbon atoms and R$_3$ represents an alkyl radical having 1 to 4 carbon atoms.

3. 2-Carbethoxy-3,4-dihydroxy-5-methyl furan.

4. 2-Carbethoxy-4-hydroxy-2,5-dimethyl-3-oxo-2H-furan.

* * * * *